United States Patent [19]

Mann

[11] Patent Number: 5,087,886
[45] Date of Patent: Feb. 11, 1992

[54] RAIN-ACTIVATED SPRINKLER SHUT-OFF SYSTEM

[76] Inventor: Harold E. Mann, 3114 E. Clarmont Ave., Phoenix, Ariz. 85016

[21] Appl. No.: 589,770

[22] Filed: Sep. 28, 1990

[51] Int. Cl.⁵ .............................................. G01R 27/02
[52] U.S. Cl. ..................... 324/696; 324/693; 324/694; 340/602
[58] Field of Search ............... 324/691, 693, 694, 696, 324/71.2, 444; 340/602

[56] References Cited

U.S. PATENT DOCUMENTS

| | | | |
|---|---|---|---|
| 2,606,748 | 8/1952 | Glegg | 324/693 X |
| 2,721,101 | 9/1953 | Richard, Jr. | 324/694 X |
| 3,968,428 | 7/1976 | Numoto | 324/694 |
| 4,120,166 | 10/1978 | Brooks, Jr. | 324/696 X |
| 4,122,389 | 10/1978 | Haagen | 324/694 |
| 4,137,931 | 2/1979 | Hasenbeck | 324/696 X |
| 4,216,789 | 8/1980 | Hasenbeck | 324/696 X |
| 4,513,608 | 4/1985 | Cuming | 324/696 X |
| 4,531,087 | 7/1985 | Larson | 324/696 |
| 4,703,253 | 10/1987 | Strommen | 324/700 |
| 4,703,255 | 10/1987 | Strommen | 324/700 |
| 4,853,614 | 8/1989 | Carver | 324/689 X |
| 4,942,354 | 7/1990 | Miller | 324/71.2 |

Primary Examiner—Kenneth A. Wieder
Assistant Examiner—Glenn W. Brown
Attorney, Agent, or Firm—Cahill, Sutton & Thomas

[57] ABSTRACT

A moisture detecting system employs a body of porous concrete with electrodes embedded therein. The body of concrete is contained within a housing having an opening in the top thereof to admit rain. The body may also have electrical probes therein connected to the electrodes, which probes can be embedded in the ground to detect moisture therein.

5 Claims, 2 Drawing Sheets

RAIN-ACTIVATED SPRINKLER SHUT-OFF SYSTEM

TECHNICAL FIELD

This invention is concerned with detecting the presence of rain water and temporarily turning off an automatic sprinkler system.

BACKGROUND ART

Timer controlled automatic sprinkler systems are in common use today both for residential and commercial properties. The controllers for these systems can be programmed to automatically turn the sprinkler on and off at certain times of the day and certain days of the week.

In order to reduce the unnecessary consumption of water it is desirable to preclude the sprinkler from being turned on during and for a period of time following a rain. Most controllers are equipped with a manual switch to accomplish this, but operators frequently forget or simply neglect to manipulate the rain switch.

There is a need for a system for automatically precluding the sprinkler system from operating during and for a predetermined time following each rain.

DISCLOSURE OF THE INVENTION

This invention provides a moisture detecting system utilizing a body of porous concrete having electrodes embedded therein. The body is in a housing having an opening in its top to admit rain water. The presence of water in the concrete block significantly increases the conductivity of the block allowing the current to flow between the electrodes. Electrical circuitry is provided for detecting the current flow between the electrodes and for turning off the sprinkler system. After the rain has stopped and the concrete block dries out, the sprinkler system is again activated.

BRIEF DESCRIPTION OF THE DRAWINGS

The invention is described in greater detail hereinafter by reference to the accompanying drawings wherein.

BEST MODES FOR CARRYING OUT THE INVENTION

Figure 1:
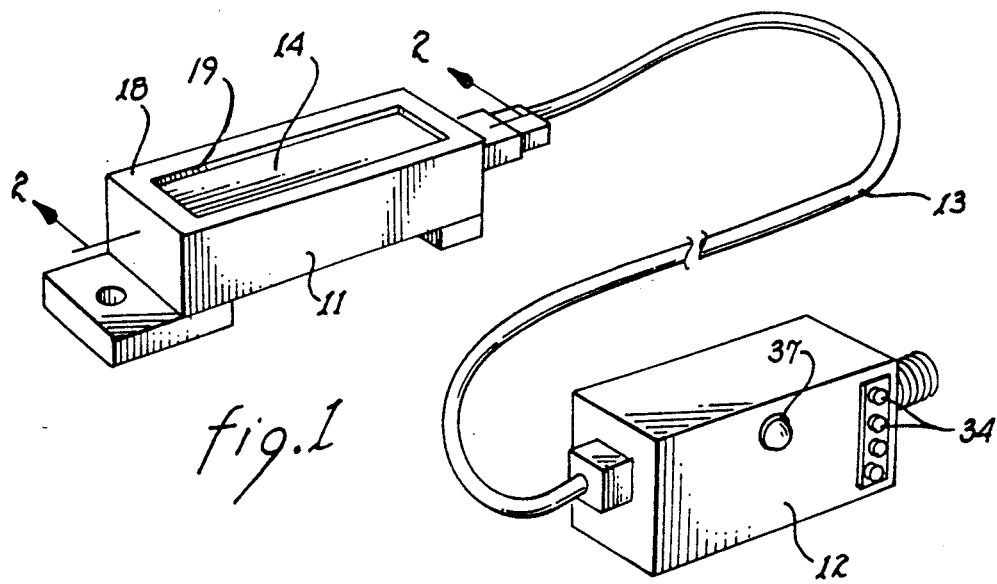
FIG. 1 is a perspective view of moisture sensing apparatus embodying this invention.

Referring particularly to FIG. 1 the apparatus there illustrated comprises a sensor unit 11 and a control box 12 electrically connected together by a cord containing electrical leads 13.

Figure 2:
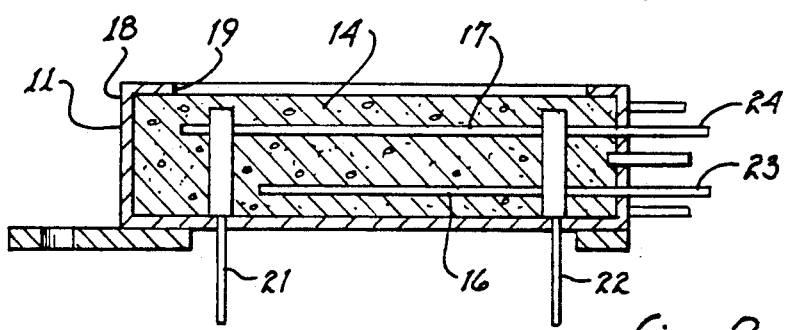
FIG. 2 is an enlarged sectional view through the moisture detecting unit of the invention.

Construction of the sensor unit 11 is shown in FIG. 2. This unit comprises a body of porous concrete 14 having a pair of electrodes 16 and 17 embedded therein. The preferred type of concrete is an expansion cement sold under the trademark Rockite by Hartline Products Company, Inc. of Cleveland, Ohio. Concrete body 14 is confined within a housing 18 having an opening 19 in the top thereof to permit rain water to fall onto the body 14.

The sensor unit may additionally include a pair of probes 21 and 22 which are connected, respectively, to electrodes 17 and 16 and which project downwardly out of housing 18. Probes 21 and 22 can be thrust into the ground to allow the sensing unit 11 to sense moisture in the ground. Probes 21 and 22 can be removed if they are not required.

Figure 3:
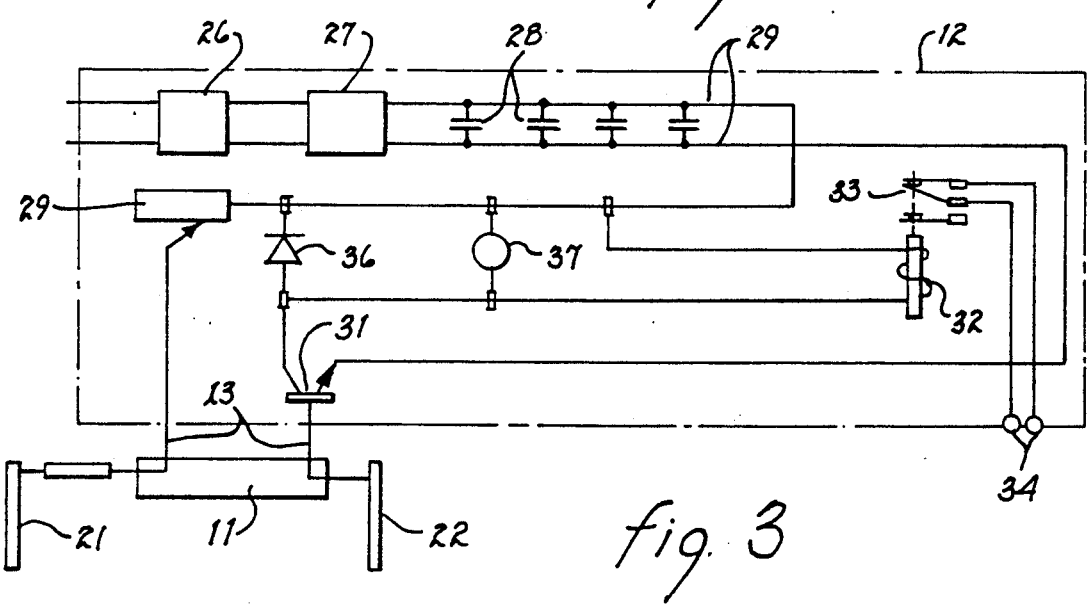
FIG. 3 is a schematic diagram of the electrical circuitry employed in the invention.

Terminals 23 and 24 projecting from sensor unit 11 and connected to electrodes 16 and 17 provide a means for electrically connecting the sensor unit to leads 13 and the electrical circuitry in control box 12. That circuitry is schematically illustrated in FIG. 3.

Household alternating current from a suitable source (not shown) is converted to low voltage direct current by means of a transformer 26 and a full wave rectifier 27. If desired, a series of capacitors 28 may be connected across output leads 29 to level any ripple in the output from the rectifier.

Sensor unit 11 is connected to the circuitry in control box 12 by leads 13 to a variable resistor 29 and to the base of a transistor 31. Voltage impressed on the base of transistor 31 is determined by the conductivity of sensor unit 11. When the concrete body 14 in sensor unit 11 is dry the resistance to current flow through sensor unit 11 is very high. If body 14 is wetted by rain or if probes 21 and 22 are in moist dirt the resistance of unit 11 drops dramatically raising the voltage beyond the threshold of transistor 31 and causing it to conduct. The voltage to the transistor can be calibrated or adjusted by means of variable resistor 29.

Transistor 31 controls the flow of current to a relay 32 containing a switch 33 in a sprinkler control circuit including terminals 34 on the outside of control box 12. When relay 32 is energized it opens switch 33 interrupting the sprinkler system circuit.

The circuitry in control box 12 may further include a diode 36 to insure unidirectional current flow to relay 32 and an LED 37 to signal that the relay 32 is energized and the sprinkler system interrupted.

Figure 5:
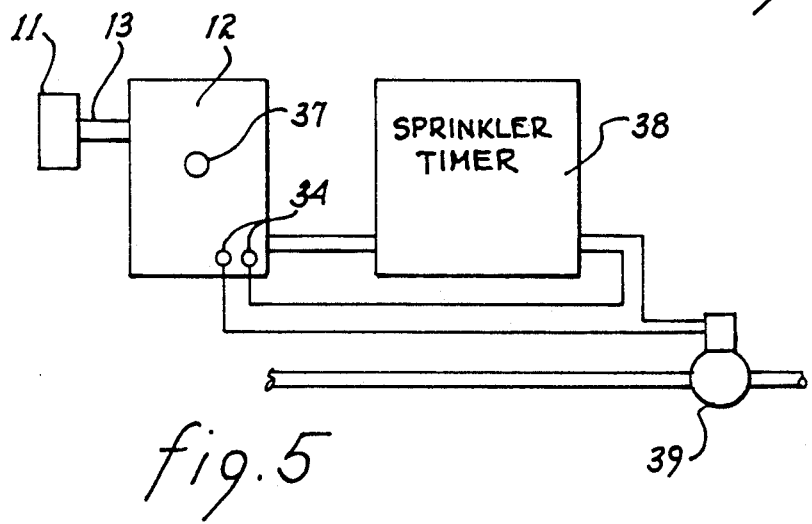
FIG. 5 is a diagram depicting connection of the moisture detecting system to an automatic sprinkler system.

Utilization of the moisture sensing apparatus is illustrated in FIG. 5. Control box 12 is connected by terminals 34 into the circuit between a sprinkler system timer 38 and a solenoid valve 39 in the sprinkler piping. When sensor unit 11 detects moisture, control box circuitry opens the sprinkler valve circuit preventing the sprinkler from being activated.

Figure 4:
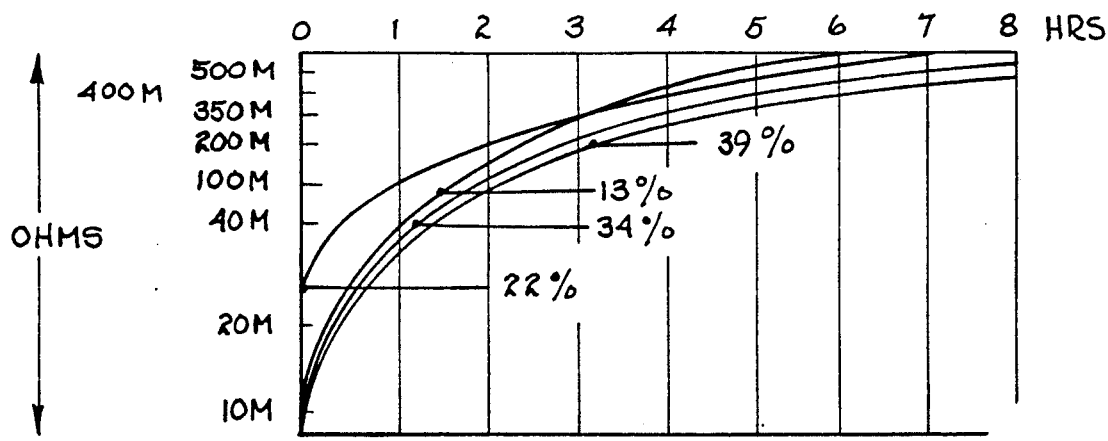
FIG. 4 is a graph depicting drying times for the moisture detecting body.

When the rain stops and concrete body 14 in sensor unit 11 begins to dry up its resistance increases gradually and eventually causes the transistor 31 to stop conducting thereby deenergizing relay 32. It preferably takes several hours for the sprinkler circuit to be reestablished. FIG. 4 illustrates the drawing resistance increase experienced by sensor unit 11 under various conditions of relative humidity. Obviously, with higher humidity the drying process in body 14 is slowed.

Figure 6:
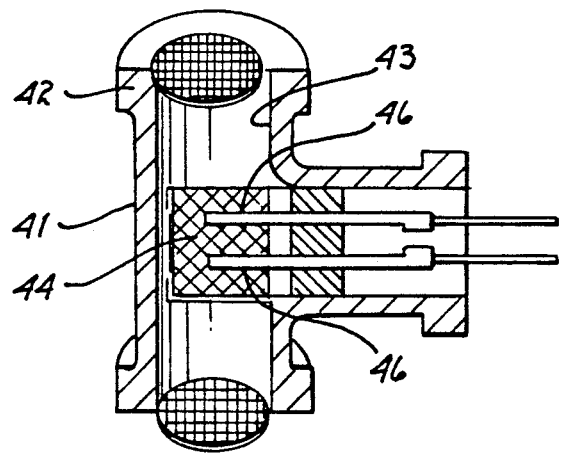
FIG. 6 is a sectional view through a moisture detecting unit having a different housing.

FIG. 6 depicts a sensor unit 41 having a different configuration for its housing 42. This housing has a vertical bore 43 in which is positioned a concrete body 44. As in the previously described embodiment, the concrete body 44 has a pair of electrodes 46 embedded therein. The through bore 43 in housing 42 gives this unit more predictable drying characteristics and hence better control over the time period that the sprinkler system is turned off after a rain.

What is claimed is:

1. A sprinkler shut-off system comprising a sensor unit exposed to the atmosphere for sensing the presence of rain water, said sensor unit having a body of porous concrete therein adapted to be wetted by rain water, a pair of electrodes embedded in said concrete body, electrical circuitry including said electrodes for sensing the conductivity of said concrete body, a control for the sprinkler, and means for shutting off the control when said electrical circuitry senses an increase in conductivity of said concrete body as a result of wetting of said body by rain water and for turning said control back on when said electrical circuitry senses a decrease in the conductivity of said concrete body as a result of drying of said concrete body in the absence of rain water.

2. The system of claim 1 further comprising a pair of electrically conducting probes connected electrically respectively to said pair of electrodes, said probes projecting beyond said body to be inserted into the ground.

3. The system of claim 2 further characterized in that said probes are removable from said body.

4. The system of claim 1 further comprising a housing for said body, said housing having an opening on the top thereof to admit rain water to said body.

5. The system of claim 1, further characterized in that the concrete body is formed from an expansion cement.

* * * * *